US012782340B2

(12) United States Patent
Schulat et al.

(10) Patent No.: US 12,782,340 B2
(45) Date of Patent: Nov. 3, 2026

(54) METHODS OF HEMATOCRIT CORRECTION AS WELL AS GLUCOSE METERS AND SYSTEMS ADAPTED THEREFOR

(71) Applicant: Roche Diabetes Care, Inc., Indianapolis, IN (US)

(72) Inventors: Jochen Schulat, Mannheim (DE); Sebastian Trick, Mannheim (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 0 days.

(21) Appl. No.: 17/466,741

(22) Filed: Sep. 3, 2021

(65) Prior Publication Data

US 2021/0396740 A1 Dec. 23, 2021

Related U.S. Application Data

(60) Division of application No. 14/731,045, filed on Jun. 4, 2015, now Pat. No. 11,137,389, which is a (Continued)

(30) Foreign Application Priority Data

Dec. 4, 2012 (EP) .................................... 12195570

(51) Int. Cl.
*G01N 27/327* (2006.01)
*G01N 33/49* (2006.01)
(Continued)

(52) U.S. Cl.
CPC ..... *G01N 33/5094* (2013.01); *G01N 27/3274* (2013.01); *G01N 33/66* (2013.01)

(58) Field of Classification Search
CPC ............. G01N 27/413; G01N 27/3274; G01N 33/5094; G01N 33/66; G01N 27/416; G01N 33/49
(Continued)

(56) References Cited

U.S. PATENT DOCUMENTS 6,377,896 B1 4/2002 Sato et al.
6,602,469 B1 8/2003 Maus et al.
(Continued)

FOREIGN PATENT DOCUMENTS

EP 0928967 A2 7/1999
WO 20060026748 A1 3/2006

OTHER PUBLICATIONS

Hodges in JP 2009294213. English translation (Year: 2009).*

*Primary Examiner* — Rebecca M Fritchman
(74) *Attorney, Agent, or Firm* — Maschoff Brennan

(57) ABSTRACT

Methods are provided for correcting an analyte concentration measurement that may be influenced by hematocrit (HCT), especially a glucose concentration measurement. The methods include determining by means of a reference instrument a HCT reference value of a reference blood sample taken from a specific user, applying a fresh blood sample of the user on a disposable analytical test element, measuring the glucose value of the fresh blood sample by single use of the test element in a glucose meter, determining a HCT correction value using at least the HCT reference value, and adjusting the measured glucose value using the HCT correction value to receive an adjusted glucose value. Also provided are devices and system incorporating or for performing the methods.

16 Claims, 1 Drawing Sheet

Related U.S. Application Data continuation of application No. PCT/EP2013/075436, filed on Dec. 3, 2013.

(51) Int. Cl.
*G01N 33/50* (2006.01)
*G01N 33/66* (2006.01)

(58) Field of Classification Search
USPC .................................. 435/29, 287.1; 702/19
See application file for complete search history.

(56) References Cited

U.S. PATENT DOCUMENTS

| | | | |
|---|---|---|---|
| 8,287,718 B2 | 10/2012 | Shinno et al. | |
| 2004/0224205 A1 | 11/2004 | Marianowski et al. | |
| 2007/0231209 A1* | 10/2007 | Cosentino ........ | G01N 33/48771 422/68.1 |
| 2007/0231914 A1* | 10/2007 | Deng ................. | G01N 27/3274 435/287.1 |
| 2007/0270672 A1* | 11/2007 | Hayter ............. | A61B 5/150526 600/309 |
| 2008/0114228 A1 | 5/2008 | McCluskey et al. | |
| 2010/0243476 A1 | 9/2010 | Fujiwara et al. | |
| 2011/0073494 A1* | 3/2011 | Mccoll ............... | G01N 27/3274 204/403.14 |
| 2015/0268228 A1 | 9/2015 | Schulat et al. | |

* cited by examiner

METHODS OF HEMATOCRIT CORRECTION AS WELL AS GLUCOSE METERS AND SYSTEMS ADAPTED THEREFOR

CROSS-REFERENCE TO RELATED APPLICATIONS

This patent application is a divisional of U.S. patent application Ser. No. 14/731,045, filed 4 Jun. 2015, which is a continuation of International Patent Application No. PCT/EP2013/075436, filed 3 Dec. 2013, which claims priority to and the benefit of EP patent application Ser. No. 12/195,570.2, filed 4 Dec. 2012. The contents of these applications are incorporated herein by reference in their entirety.

TECHNICAL FIELD

This disclosure relates generally to engineering and medicine/medical diagnostics, and more particularly, it relates to methods of hematocrit correction in an analyte test meter, as well as test meters and systems incorporating the same.

BACKGROUND

Hematocrit (HCT) may be defined as the volume percentage (%) of red blood cells in whole blood. HCT is normally about 45% for men and 40% for women and may range from about 20% to about 70% in extreme cases. It is known that HCT can impact the glucose level of a blood sample being tested. To account for such a HCT interference, it has been proposed to additionally measure the actual HCT value of a given sample (e.g., by multiple wavelength, conductivity or other tests) in addition to the glucose test. However, such measurements imply unwanted complexity in self-testing devices and are prone to measurement uncertainty. As an alternative, efforts have been made to reduce the HCT influence by the design of the test chemistry or disposable (e.g., by retaining red blood cells through separating layers). However, such a measure can eliminate the HCT influence only to a residual dependency.

For the foregoing reasons, there is a need for improving known methods and devices for HCT correction, especially in glucose measurements, and to provide improved measurement certainty specifically in a self-testing environment without undue effort.

BRIEF SUMMARY

An inventive concept described herein includes recognizing that a mean/average HCT from a given individual (under normal life conditions) fluctuates only in a limited range and thus can be used to correct an analyte measurement influenced by the individual's HCT. This inventive concept is achieved by determining at least one HCT reference value for an individual, which can be exactly measured by use of a clinical or laboratory analyzer, whereas routine glucose measurements on test elements can be repeatedly conducted and corrected on the basis of one and the same HCT reference value without increased measurement effort. This inventive concept can be incorporated into exemplary methods, devices and systems as described herein and in more detail below.

For example, methods of HCT correction are provided that include determining by means of a reference instrument, such as a laboratory analyzer, a HCT reference value of a reference blood sample taken from a specific user.

In addition, the methods include applying a fresh blood sample of the user on a disposable analytical test element, and measuring the glucose value of the fresh blood sample by single use of the test element in the glucose meter.

Moreover, the methods include determining a HCT correction value using at least the HCT reference value, and adjusting the measured glucose value using the HCT correction value to receive an unbiased adjusted glucose value. In some instances, the determining the HCT correction value step involves using one or more correction functions or a lookup table determined empirically in connection with the architecture of the test element eventually in combination with the glucose meter.

For a convenient handling, the HCT reference value may be transferred via a wireless or wire-bound interface into a memory of the glucose meter.

For safety considerations, it is advantageous when the HCT reference value is transmitted to the glucose meter using an external software on a device outside the glucose meter that is inaccessible to the user. In some instances, the HCT reference value is stored in an external database outside the glucose meter in connection with a user identifier for the user.

For facilitating data exchange for a personalized device, the glucose meter may include machine readable means, specifically an RFID chip, for automatic user identification.

Another improvement provides that the user identity is checked by a query provided by the glucose meter, whereupon an input of a confirmation by the user is requested.

To account for eventual deviations of the HCT reference value, the user may be queried about a change in living conditions influencing HCT.

For a reliability check, it is favorable when the timeliness of the HCT reference value is verified within a given time interval.

For further awareness of the patient or user, the user can be informed that personalized data are used for correction of the measured glucose value.

To avoid unwanted loss of a test medium, the adjusted glucose value can be displayed to the user upon fulfilling given conditions including availability of the HCT reference value and optionally timeliness of this value, whereas otherwise to provide a fallback result the measured glucose value is displayed.

For improved elimination of the HCT effect when the HCT correction value is determined independent of the HCT reference value and the measured glucose value.

The HCT correction is particularly effective when the glucose value of the fresh blood sample is measured by photometric or electrochemical detection on the analytical test element.

In view of the foregoing, devices for HCT correction, such as blood glucose meters, are provided that include a means configured to receive at least one disposable test element on which a blood sample can be applied or is applied.

The devices also can include a detector adapted for measuring a blood glucose value using the at least one test element loaded with a fresh blood sample of a specific user The devices also can include an interface configured to input a HCT reference value of a reference blood sample of the user, and a processor adapted to determine a HCT correction value using the HCT reference value and the measured glucose value and to adjust the measured glucose value using the HCT correction value.

For a trusted execution of the HCT correction, it is advantageous to provide a means operable to allow HCT correction of the blood glucose measurement depending on the provision of a (valid) HCT reference value. It may also be conceivable that in case of a missing HCT reference value, an uncorrected measurement result is provided together with a corresponding indication to the user.

Systems for HCT correction also are provided that include a glucose meter as described herein and a reference instrument, such as a laboratory analyzer, to determine a HCT reference value of a reference blood sample taken from a specific user of the glucose meter.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

Figure 1:
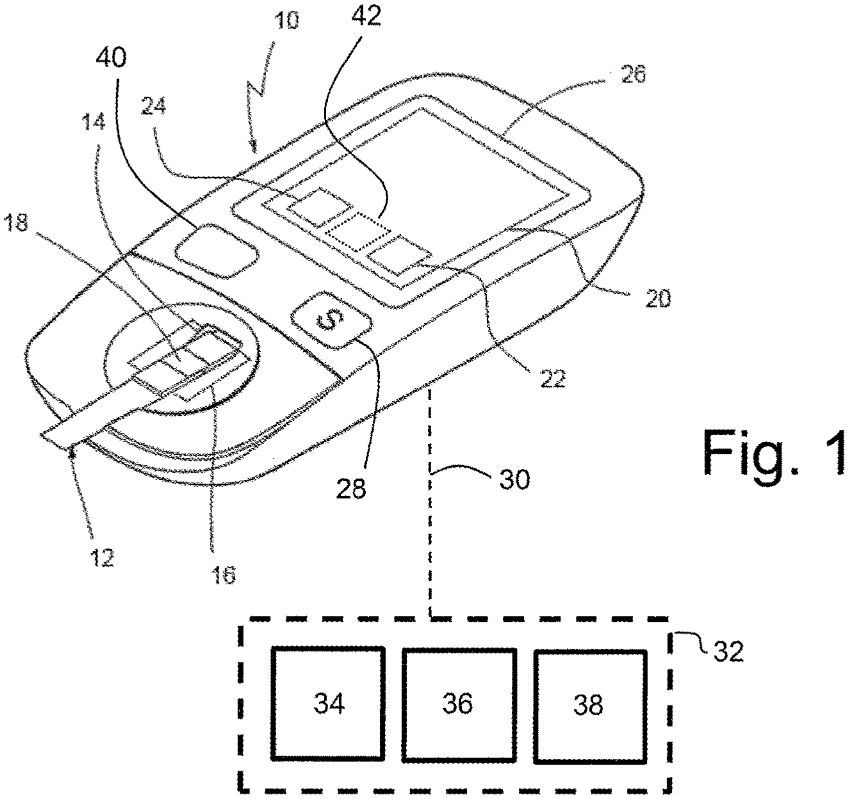
FIG. 1 is a perspective and partially schematic view of a glucose meter in connection with an external reference system for HCT correction.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The methods, devices and systems now will be described more fully hereinafter with reference to the accompanying drawings, in which some, but not all embodiments of the inventive concept are shown. Indeed, the methods, devices and systems may be embodied in many different forms and should not be construed as limited to the embodiments set forth herein; rather, these embodiments are provided so that this disclosure will satisfy applicable legal requirements.

Likewise, many modifications and other embodiments of the methods, devices and systems described herein will come to mind to one of skill in the art to which the disclosure pertains having the benefit of the teachings presented in the foregoing descriptions and the associated drawings. Therefore, it is to be understood that the methods, devices and systems are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the methods, devices and systems, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

As noted above, HCT can adversely affect electrochemical and/or photometric measurement of an analyte concentration or presence. The present disclosure addresses that problem by determining at least one HCT reference value, which can be exactly measured by use of a clinical or laboratory analyzer, whereas routine glucose measurements on test elements can be repeatedly conducted and corrected on the basis of one and the same HCT reference value without increased measurement effort. This also is due to a finding that the HCT-dependency of typical self-monitoring blood glucose monitoring systems including a given test architecture and device is relatively constant. The adjustment of the measured glucose value can be easily implemented on processors that are already included in handheld devices or home meters for other data handling purposes. Thus, device and/or system performance can be improved significantly, whereat the meter is then assigned to a specific user (i.e., as a personalized device). In this way, the HCT correction is easily feasible in a glucose monitoring system without the need for the user to bring blood samples to a laboratory for determining the glucose bias in each and every case.

Methods, Devices and Systems

FIG. 1 illustrates an exemplary handheld glucose meter 10 for insertion of a disposable test strip 12 usable by a proband or user for self-testing in an everyday environment. The meter 10 includes a holder 14 to position the test strip 12 in the optical path of a reflection-photometric detector 16 to read the reflectance of a test pad 18 of the test strip 12. A small volume of a fresh sample of whole blood taken by the user on the spot can be applied to the test pad 18, where a reagent reacts with glucose leading to a change in reflectance that is detectable from the bottom of the test pad 18 with the photometric detector 16. Such measurements are known to one of skill in the art per se and need not to be elucidated in more detail. It is further known that the HCT of a blood sample can impact the glucose level to be tested (e.g., by diffusion effects in the test pad 18).

To process and correct the measurement signals, a device electronics 20 includes a processor 22, a memory 24, a display 26 and keys 28 for interacting with the user and an interface 30 for eventual connection to an external reference system 32. The processor 22 is adapted for HCT correction using the measured glucose value and a HCT reference value initially provided through the reference system 32 and stored in the memory 24.

The HCT reference value can be determined by means of an external reference instrument 34 formed as a laboratory analyzer. For this purpose, a specific user may provide a reference blood sample to be analyzed with the reference instrument 34 in a clinical or laboratory setting. Then, the determined HCT reference value can be transmitted into the memory 24 of the glucose meter 10 via the (wireless) interface 30 using an external software 36 running on a device outside the meter 10. To ensure a safe handling, the software 36 should be inaccessible to the user and only operable by authorized personnel (e.g., by a health professional). For example, a physician may connect the glucose meter 10 of a patient to a computer in his medical practice running the software 36 such that configuration data of the meter 10 can be read out and the HCT reference value can be set only by the physician, thereby ensuring that the values are controlled and interpreted with the necessary medical knowledge and are not manipulated by a layperson or the user.

It also may be conceivable that the HCT reference value is stored in a database 38 of the reference system 32 in connection with an identifier for the user who has provided the reference sample. An automatic data transfer to the glucose meter 10 assigned to the user could then be accomplished by an identification process enabled by machine readable means, specifically an RFID chip 40 mounted on the meter 10 and containing the user identifier.

It should be emphasized that such an initial procedure is only necessary once in a while, as the HCT value of a given individual is usually relatively constant over time. Given the living situation does not change, the HCT value of an individual typically fluctuates by less than 2%, which is small compared to the possible range of HCT values for different persons (typically about 20% to about 55%, eventually up to about 70% in certain disease states).

By storing the HCT reference, the meter 10 is personalized for the specific user and can be employed for glucose measurements in a daily routine. To carry out such a measurement, the user takes a fresh blood sample and applies it on the test strip 12 before or after insertion into the meter 10, in which a glucose value can be measured automatically by means of the detector 16. At the beginning of the measurement routine, the user identity is checked (e.g., by a query displayed to the user on the display 26 and requesting input of a confirmation by means of keys 28). The user can be informed by an indication on the display 26 that personalized data are used for correction of the glucose measurement. The user may further be queried about a change in living conditions that may influence HCT such as, for example, training in higher altitudes.

The processing routine also may include a verification of the timeliness of the HCT reference value, which should be updated regularly (e.g., once in a year).

The meter 10 may include an activation stage 42 (e.g., in the form of a software routine or input field) to allow a glucose measurement only if a valid HCT reference value is available. The validity and specifically the attribution to a specific user may be proved by a security query to be confirmed by the user. Alternatively, in case of a missing HCT reference value, the processing routine could provide the measured glucose value to the user together with information that no correction has been made.

If a valid HCT reference value is stored in the memory 24, the HCT correction value is determined in dependence of the HCT reference value and the measured glucose value. Then, the measured glucose value is adjusted using the HCT correction value to receive an adjusted glucose value unbiased by HCT.

The measured glucose concentration can be corrected in consideration of the HCT reference value by using one or more correction functions. For example, a correction function in the form of a correction equation may be used, in which one or more correction factors and/or one or more correction offsets are used. It has been found that the correction of the measured glucose concentration C(meas) can be effected for example according to the following equation:

$$C(\text{corr})=C(\text{meas})+m*HCT^{i}+n \quad (1).$$

In this equation, HCT is the hematocrit reference value, C(meas) is the measured glucose concentration, C(corr) is the corrected glucose concentration, and the factor m and the exponent i are experimentally or empirically determined correction parameters, which may, for example, depend on the temperature and the concentration of glucose itself.

Figure 2:
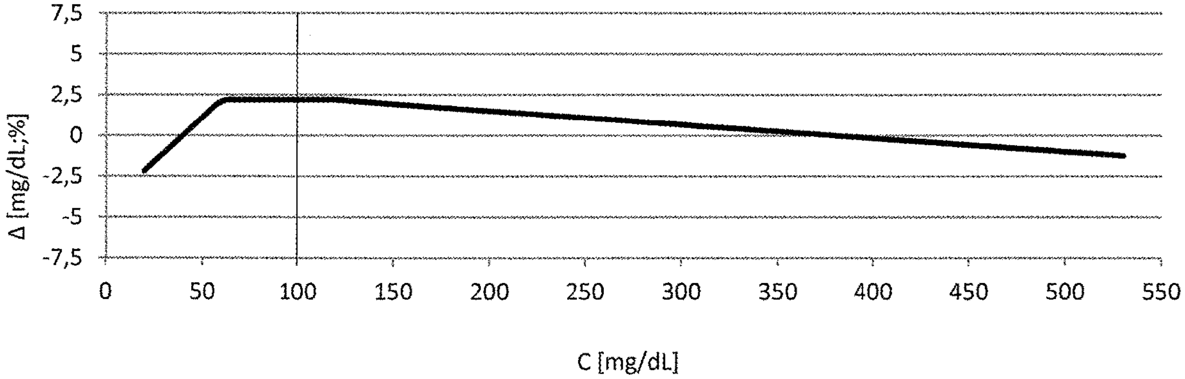
FIG. 2 is a plot of HCT-induced glucose bias Δ versus the glucose concentration C for a given HCT value.

FIG. 2 illustrates the deviation Δ of the measured glucose concentrations from the actual glucose concentrations C(ref) determined by a means of a reliable reference method. The uncorrected glucose concentration could be measured using the handheld glucose meter 10, and the actual glucose concentrations could be determined using a laboratory device, or in other ways. For a sample with HCT of 30% the horizontal axis in FIG. 2 denotes the measured glucose concentrations C in milligram per deciliter, and the vertical axis shows the deviation Δ. For glucose concentrations below 100 mg/dL the deviations Δ are given as absolute values in mg/dL, whereas for glucose concentrations above 100 mg/dL, the deviations Δ are given as a percentage.

Such curves or polygons can be determined for a plurality of HCTs and glucose levels, such that the curves can be put together to a hypersurface, wherein for example, the measured glucose concentration is plotted on a first axis, the HCT on a second axis, and the deviation Δ on a third axis. Such hypersurfaces can be stored in the memory 24 for example as individual values in a lookup table or being defined analytically or in other ways, such that in each case for each HCT value and each measured glucose concentration, the corresponding deviation Δ can be easily deducted with the processor 22 to provide a corrected value of the glucose concentration. It has been found that the HCT dependency largely is stable over different batches of test strips 12. The HCT correction values determined are therefore generally valid for a combination of a meter 10 and a test strip 12 or other test element having a specific test chemistry.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

LISTING OF REFERENCE NUMBERS

10 handheld glucose meter
12 disposable test strip
14 holder
16 reflection-photometric detector
18 test pad
20 device electronics
22 processor
24 memory
26 display
28 keys
30 interface
32 external reference system
34 external reference instrument
36 external software
38 database
40 RFID chip
42 activation stage

The invention claimed is:

1. A glucose meter, comprising:

a. a holder configured to receive at least one disposable test element on which a blood sample can be applied or is applied;

b. a detector configured to measure a blood glucose value using the test element loaded with a fresh blood sample of a specific user and provide a measured blood glucose value, wherein the test element is an electrochemical-based test element or a photometric-based test element and the detector is an electrochemical-based detector or a photometric-based detector;

c. an interface configured to input or receive a memory and a predetermined hematocrit reference value stored in the memory, wherein the predetermined hematocrit reference value is determined from a reference blood sample of said user, wherein the fresh blood sample and the reference blood sample are distinct from each other; and d. a processor configured to:

control operation of the detector to generate a glucose measurement signal from the test element;

determine a hematocrit correction value representative of a hematocrit-dependent measurement bias of the detector, the hematocrit correction value being determined as a function of the predetermined hematocrit reference value;

apply the hematocrit correction value to the glucose measurement signal to generate a hematocrit-compensated glucose value that reduces detector bias attributable to hematocrit variation; and display the hematocrit-compensated glucose value on a display of the glucose meter;

wherein the predetermined hematocrit reference value is used for repeated user-specific modification of glucose values to compensate for detector bias attributable to hematocrit variation across a plurality of glucose measurements.

2. The glucose meter of claim 1, wherein the processor is further configured to apply the hematocrit correction value to the measured blood glucose value dependent on if the predetermined hematocrit reference value is received.

3. The glucose meter of claim 1, wherein the glucose meter is a handheld device usable for self-testing on the spot.

4. The glucose meter of claim 1, wherein the detector is a photometric detector.

5. The glucose meter of claim 4, wherein the test element is positionable in an optical path of the photometric detector.

6. The glucose meter of claim 1, wherein the processor is further configured to display a user identification confirmation request on the display at the beginning of a measurement routine.

7. The glucose meter of claim 1, wherein the processor is further configured to prevent a glucose measurement if the predetermined hematocrit reference value is unavailable.

8. The glucose meter of claim 1, wherein the processor is further configured to display a glucose value to which the hematocrit correction value is not applied, and an indication the hematocrit correction value is not applied to the glucose value, on a display of the glucose meter if the predetermined hematocrit reference value is unavailable.

9. The glucose meter of claim 1, further comprising an RFID chip containing a user identifier.

10. The glucose meter of claim 9, wherein the interface memory automatically receives the predetermined hematocrit reference value in response to a database identification of the RFID.

11. The glucose meter of claim 1, wherein the processor is further configured to determine if the predetermined hematocrit reference value was input to or received by the interface memory within a predetermined period of time.

12. A system comprising:

the glucose meter of claim 1; and a reference instrument to determine the predetermined hematocrit reference value of a reference blood sample taken from a specific user of the glucose meter.

13. The system of claim 12, wherein the reference instrument is a laboratory analyzer.

14. A glucose meter, comprising:

a. a holder configured to receive at least one disposable test element on which a blood sample can be applied or is applied;

b. a detector configured to measure a blood glucose value using the test element loaded with a fresh blood sample of a specific user and provide a measured blood glucose value, wherein the test element is an electrochemical-based test element or a photometric-based test element and the detector is an electrochemical-based detector or a photometric-based detector;

c. an interface configured to input or receive a predetermined hematocrit reference value of a reference blood sample of said user to a memory configured to store said predetermined hematocrit reference value, said predetermined hematocrit reference value being determined by an external reference instrument, wherein the fresh blood sample and the reference blood sample are distinct from each other; and d. a processor configured to:

control operation of the detector to generate a glucose measurement signal from the test element;

determine a hematocrit correction value as a function of the predetermined hematocrit reference value and the glucose measurement, the hematocrit correction value being representative of a hematocrit-dependent measurement bias of the detector;

apply the hematocrit correction value to the glucose measurement signal to generate obtain an adjusted glucose value accounting for hematocrit bias by modifying the measured blood glucose value to account for the deviation a hematocrit-compensated glucose value that reduces detector bias attributable to hematocrit variation; and display the hematocrit-compensated glucose value on a display of the glucose meter;

wherein the predetermined hematocrit reference value is used for repeated user-specific modification of glucose values to compensate for detector bias attributable to hematocrit variation across a plurality of glucose measurements.

15. The glucose meter of claim 14, wherein the interface is configured to wirelessly receive the hematocrit reference value.

16. The glucose meter of claim 14, wherein the processor is further configured to determine if the predetermined hematocrit reference value was input to or received by the interface within a predetermined period of time.

* * * * *